US010328205B2

(12) United States Patent
Stefanov (10) Patent No.: US 10,328,205 B2
(45) Date of Patent: Jun. 25, 2019

(54) DRUG DELIVERY DEVICE WITH PNEUMATIC POWER PACK

(71) Applicant: Carebay Europe Ltd., Silema (MT)

(72) Inventor: Slobodan Stefanov, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 244 days.

(21) Appl. No.: 15/204,187

(22) Filed: Jul. 7, 2016

(65) Prior Publication Data

US 2018/0008775 A1  Jan. 11, 2018

(51) Int. Cl.
 *A61M 5/20* (2006.01)
 *A61M 5/24* (2006.01)
 (Continued)

(52) U.S. Cl.
 CPC ............ *A61M 5/2053* (2013.01); *A61M 5/24* (2013.01); *A61M 5/31511* (2013.01); *A61M 5/31576* (2013.01); *A61M 5/31583* (2013.01); *A61M 5/31591* (2013.01); *A61M 5/3202* (2013.01); *A61M 2005/208* (2013.01); *A61M 2005/3128* (2013.01); *A61M 2005/3267* (2013.01)

(58) Field of Classification Search
 CPC ........ A61M 2005/3247; A61M 5/2053; A61M 5/31511; A61M 5/31576; A61M 5/31583
 See application file for complete search history.

(56) References Cited

U.S. PATENT DOCUMENTS 2,605,763 A   8/1952 Smoot
4,518,384 A * 5/1985 Tarello .................... A61M 5/20
                                                            604/61
(Continued)

FOREIGN PATENT DOCUMENTS

CN     1909939 A     2/2007
CN   104968381 A1   10/2015
(Continued)

OTHER PUBLICATIONS

International Search Report issued in International Application No. PCT/EP2017/066263 dated Oct. 20, 2017.
(Continued)

*Primary Examiner* — Rebecca E Eisenberg
*Assistant Examiner* — Tasnim Mehjabin Ahmed
(74) *Attorney, Agent, or Firm* — McDonnell Boehnen Hulbert & Berghoff LLP (57) ABSTRACT

A drug delivery device configured to provide a dose of medicament is disclosed. The drug delivery device includes a main housing, a syringe arranged in the main housing, and a pneumatic power pack arranged in the main housing. The pneumatic power pack includes a pressurized gas source storing pressurized gas, a valve for the pressurized gas source, a sleeve having an inner wall, and a plunger. The sleeve is configured to receive pressurized gas released from the pressurized gas source. The plunger is in sliding gas-tight engagement with the inner wall of the sleeve. Upon activation of the valve, the valve releases the pressurized gas, and the released pressurized gas flows into the sleeve and propels the plunger in a distal direction with respect to the sleeve and the syringe, so as to eject medicament from the syringe.

18 Claims, 7 Drawing Sheets

(51) Int. Cl.
  *A61M 5/32* (2006.01)
  *A61M 5/315* (2006.01)
  *A61M 5/31* (2006.01)

(56) References Cited

U.S. PATENT DOCUMENTS

| | | | | |
|---|---|---|---|---|
| 5,383,851 | A * | 1/1995 | McKinnon, Jr. | A61M 5/30 604/143 |
| 5,478,316 | A * | 12/1995 | Bitdinger | A61M 5/2033 604/134 |
| 5,891,086 | A * | 4/1999 | Weston | A61M 5/30 604/143 |
| 6,830,560 | B1 | 12/2004 | Gross et al. | |
| 7,207,967 | B1 * | 4/2007 | Bellhouse | A61M 5/3015 604/68 |
| 7,635,356 | B2 | 12/2009 | Stamp | |
| 7,654,983 | B2 | 2/2010 | De la Serna et al. | |
| 7,776,015 | B2 | 8/2010 | Sadowski et al. | |
| 8,002,753 | B2 | 8/2011 | Krumme et al. | |
| 9,987,436 | B2 | 6/2018 | Giambattista et al. | |
| 2002/0123717 | A1 * | 9/2002 | Landau | A61M 5/30 604/70 |
| 2005/0165360 | A1 * | 7/2005 | Stamp | A61M 5/2033 604/187 |
| 2014/0018729 | A1 * | 1/2014 | Foster | A61M 5/3015 604/58 |

FOREIGN PATENT DOCUMENTS

| | | |
|---|---|---|
| EP | 1476210 B1 | 9/2008 |
| EP | 2624887 B1 | 1/2015 |
| GB | 2410188 A | 7/2005 |
| WO | 2014095424 A1 | 6/2014 |

OTHER PUBLICATIONS

Search Report issued in Chinese Patent Application No. 106122080 dated Jul. 25, 2018.
English Translation of Abstract of WO 2014/095525 dated Nov. 15, 2018.

* cited by examiner

DRUG DELIVERY DEVICE WITH PNEUMATIC POWER PACK

FIELD OF THE PRESENT PATENT APPLICATION

This present disclosure relates to relates to drug delivery devices such as automatic injection devices.

BACKGROUND

Unless otherwise indicated herein, the materials described in this section are not prior art to the claims in this application and are not admitted to be prior art by inclusion in this section.

In some situations, it is desirable for patients to be able to administer drugs and medicament by themselves, e.g., without the need for trained medical staff to administer the drugs. There are a number of different existing delivery devices with varying degrees of automatic functions. For instance, existing automatic injection devices provide a means for automatically propelling a plunger forward to eject medicament from the automatic injection device in response to activation of the device.

In existing devices, the means for automatically propelling the plunger forward to eject the medicament are often complex and expensive to manufacture. There is, therefore, a desire to reduce the cost of manufacturing automatic injection devices while maintaining the reliability of the injection device to eject the dose of medicament.

Further, for some types of medicaments, there is a desire to eject the medicament at a substantially constant force. However, certain existing devices for ejecting the medicament at a substantially constant force are complex and expensive to manufacture. There is a desire to reduce the cost of manufacturing automatic injection devices while maintaining the reliability of the injection device to eject the medicament at a substantially constant force.

SUMMARY

A drug delivery device configured to administer a dose of medicament is provided. In an example embodiment, the drug delivery device includes a main housing, a syringe arranged in the main housing, and a pneumatic power pack arranged in the main housing. The syringe holds a medicament. The pneumatic power pack includes: (i) a pressurized gas source storing pressurized gas; (ii) a valve for the pressurized gas source; (iii) a sleeve having an inner wall, wherein the sleeve is configured to receive pressurized gas released from the pressurized gas source; and (iv) a plunger axially movable with respect to both the sleeve and the syringe. The plunger is in sliding gas-tight engagement with the inner wall of the sleeve. Upon activation of the valve, the valve releases the pressurized gas, and the released pressurized gas flows into the sleeve and propels the plunger in a distal direction with respect to the sleeve and the syringe, so as to eject the medicament from the syringe.

In another example embodiment, the drug delivery device includes a main housing, a medicament container arranged in the main housing, a needle cover axially movable with respect to the main housing, and a pneumatic power pack arranged in the main housing. The medicament container holds a medicament. The pneumatic power pack includes: (i) a pressurized gas source having a valve and storing pressurized gas; (ii) a sleeve having an inner wall, wherein the sleeve is axially moveable with respect to the main housing; and (iii) a plunger comprising an inner chamber. The plunger is axially movable with respect to both the sleeve and the medicament container. Further, the plunger is in sliding gas-tight engagement with the inner wall of the sleeve. Still further, the sleeve and the inner chamber are configured to receive pressurized gas released from the pressurized gas source. Axial movement of the needle cover in a proximal direction causes axial movement of the sleeve in the proximal direction, and the axial movement of the sleeve in the proximal direction activates the valve to release the pressurized gas. The released pressurized gas flows into both the sleeve and the inner chamber and propels the plunger in a distal direction with respect to the sleeve and the medicament container, so as to eject the medicament from the medicament container.

In still yet another example embodiment, the drug delivery device includes a main housing, a medicament container arranged in the main housing, and a pneumatic power pack arranged in the main housing. The medicament container holds a medicament. The pneumatic power pack includes: (i) a pressurized gas source storing pressurized gas; (ii) a valve for the pressurized gas source; (iii) a sleeve having an inner wall; and (iv) a plunger comprising an inner chamber and a pressure release valve configured to release pressure from the inner chamber when the pressure in the inner chamber reaches a threshold pressure level. The plunger is axially movable with respect to both the sleeve and the medicament container. Further, the plunger is in sliding gas-tight engagement with the inner wall of the sleeve. The sleeve and the inner chamber are configured to receive pressurized gas released from the pressurized gas source. The valve for the pressurized gas source is configured to release the pressurized gas upon activation of the valve. Further, the released pressurized gas flows into both the sleeve and inner chamber and propels the plunger in a distal direction with respect to the sleeve and the medicament container at a substantially constant force, so as to eject the medicament from the medicament container.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

Exemplary embodiments are described herein with reference to the drawings, in which.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The methods and systems in accordance with the present disclosure beneficially provide improved methods and systems for propelling a plunger forward so as to eject the medicament from an automatic injection device. The disclosed methods and systems provide a reliable, intuitive, and user-friendly drug delivery device that uses a pressurized gas to eject a dose of medicament. Further, the disclosed methods and systems provide a cost effective means for propelling the plunger forward so as to eject the medicament and thus help to reduce the cost of manufacturing automatic injection devices.

In accordance with an example embodiment of the present disclosure, a drug delivery device includes a main housing, a syringe arranged in the main housing, and a pneumatic power pack arranged in the main housing. The syringe holds a dose of medicament. The pneumatic power pack includes a pressurized gas source storing pressurized gas, a valve for the pressurized gas source, a sleeve having an inner wall, and a plunger. The sleeve is in gas-tight engagement with the pressurized gas source and is configured to receive pressurized gas released from the pressurized gas source. The plunger is at least partly surrounded by the sleeve and is axially movable with respect to both the sleeve and the syringe. Further, the plunger is in sliding gas-tight engagement with the inner wall of the sleeve. Upon activation of the valve, the valve releases the pressurized gas. The released pressurized gas then flows into the sleeve and propels the plunger in a distal direction with respect to the sleeve and the syringe, so as to eject the medicament from the syringe.

In an example embodiment, the plunger includes an inner chamber for receiving the released pressurized gas. In this embodiment, upon activation of the valve, the released pressurized gas flows into both the sleeve and the inner chamber. This pressurized gas then propels the plunger in the distal direction with respect to the sleeve and the syringe, so as to eject the medicament from the syringe.

Figure 1:
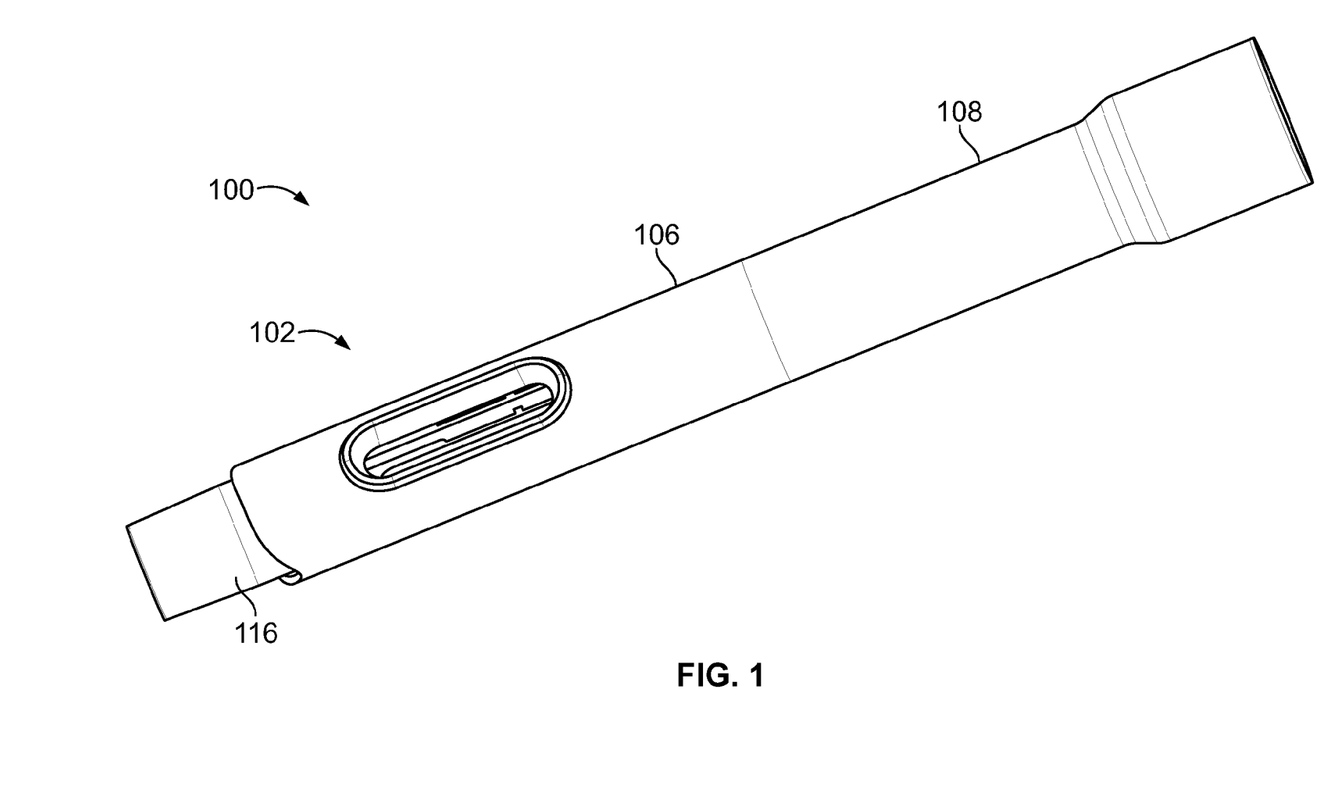
FIG. 1 illustrates a perspective view of an example drug delivery device having an example pneumatic power pack, according to an example embodiment of the present disclosure.

FIG. 1 generally illustrates an example drug delivery device that uses pressurized gas to deliver a dose of medicament. In particular, FIG. 1 illustrates a drug delivery device 100 in an initial state prior to injection. Further, FIG. 2 illustrates an exploded view of the components of the drug delivery device 100 in the initial state prior to injection.

Figure 2:
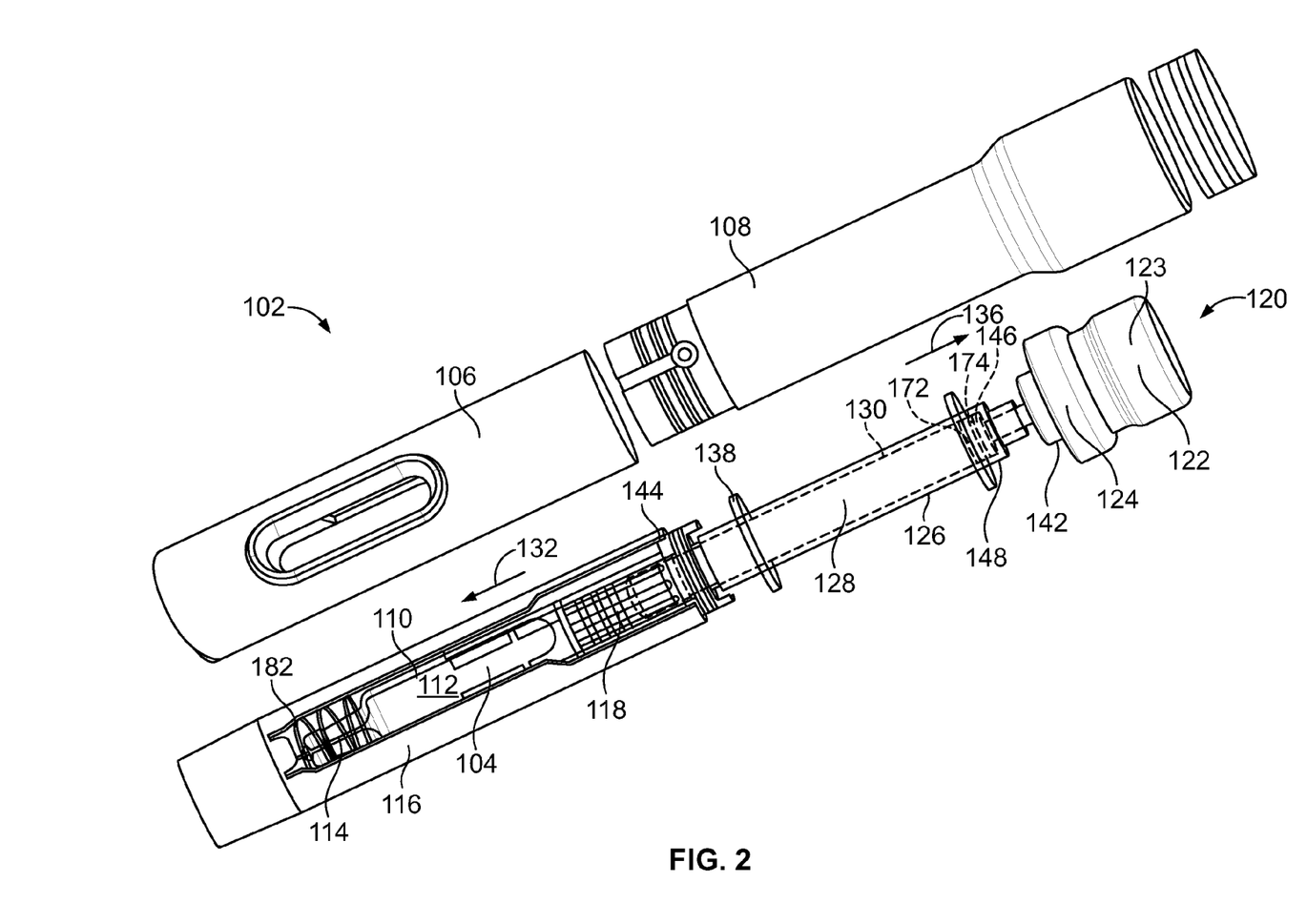
FIG. 2 illustrates an exploded, perspective view of example components of the drug delivery device of FIG. 1 in an initial state prior to injection, according to an example embodiment of the present disclosure.

As seen in FIGS. 1 and 2, drug delivery device 100 includes a main housing 102 and a syringe 104 arranged in the main housing 102. Main housing 102 includes a first housing portion 106 and a second housing portion 108. First and second housing portions 106, 108 include corresponding engagement features for providing an engagement between the two housing portions 106, 108. In an example embodiment, during assembly of the drug delivery device 100, the first and second housing portions are irreversibly attached to one another. Although main housing 102 is depicted as comprising first and second housing portions 106, 108, in other examples, main housing 102 may comprise more or fewer portions. For instance, in an example embodiment, the main housing 102 is of unitary construction.

With reference to FIG. 2, the syringe 104 includes a syringe body 110 holding a medicament 112, a needle 114, and a needle cover 116 covering the needle 114. A piston or stopper 118 is disposed in the syringe body 110. The drug delivery device 100 further includes a pneumatic power pack 120 for ejecting the medicament from the syringe 104. The pneumatic power pack 120 includes a pressurized gas source 122 storing pressurized gas 123, a valve 124 for the pressurized gas source 122, a sleeve 126, and a plunger 128.

The sleeve 126 is in gas-tight engagement with the pressurized gas source 122 and is configured to receive pressurized gas 123 released from the pressurized gas source 122. As used herein, "gas-tight engagement" means an engagement providing a seal that prevents or substantially prevents leakage of gas through the seal during the dose delivery process. By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide. In an example embodiment, the gas-tight engagement prevents or limits leakage of gas such that less than 0.5% of the released pressurized gas 123 received in sleeve 126 is able to leak through the gas-tight engagement during the dose delivery process. In another example embodiment, the gas-tight engagement prevents or limits leakage of gas such that less than 1% of the released pressurized gas 123 received in sleeve 126 is able to leak through the gas-tight engagement during the dose delivery process. In yet another example, the gas-tight engagement prevents or limits leakage of gas such that less than 5% of the released pressurized gas 123 received in sleeve 126 is able to leak through the gas-tight engagement during the dose delivery process.

The sleeve 126 has an inner wall 130, and the plunger 128 is in sliding gas-tight engagement with the inner wall 130 of the sleeve 126. During an injection process of drug delivery device 100, the pressurized gas 123 will axially move the plunger 128 with respect to the sleeve 126 and consequently with respect to the syringe 104. In particular, upon activation of valve 124, the valve 124 releases the pressurized gas 123. The pressurized gas 123 then flows into the sleeve 126 and propels the plunger 128 in distal direction 132 with respect to the sleeve 126 and syringe 104, so as to eject the medicament from the syringe 104 through needle 114.

Figure 3:
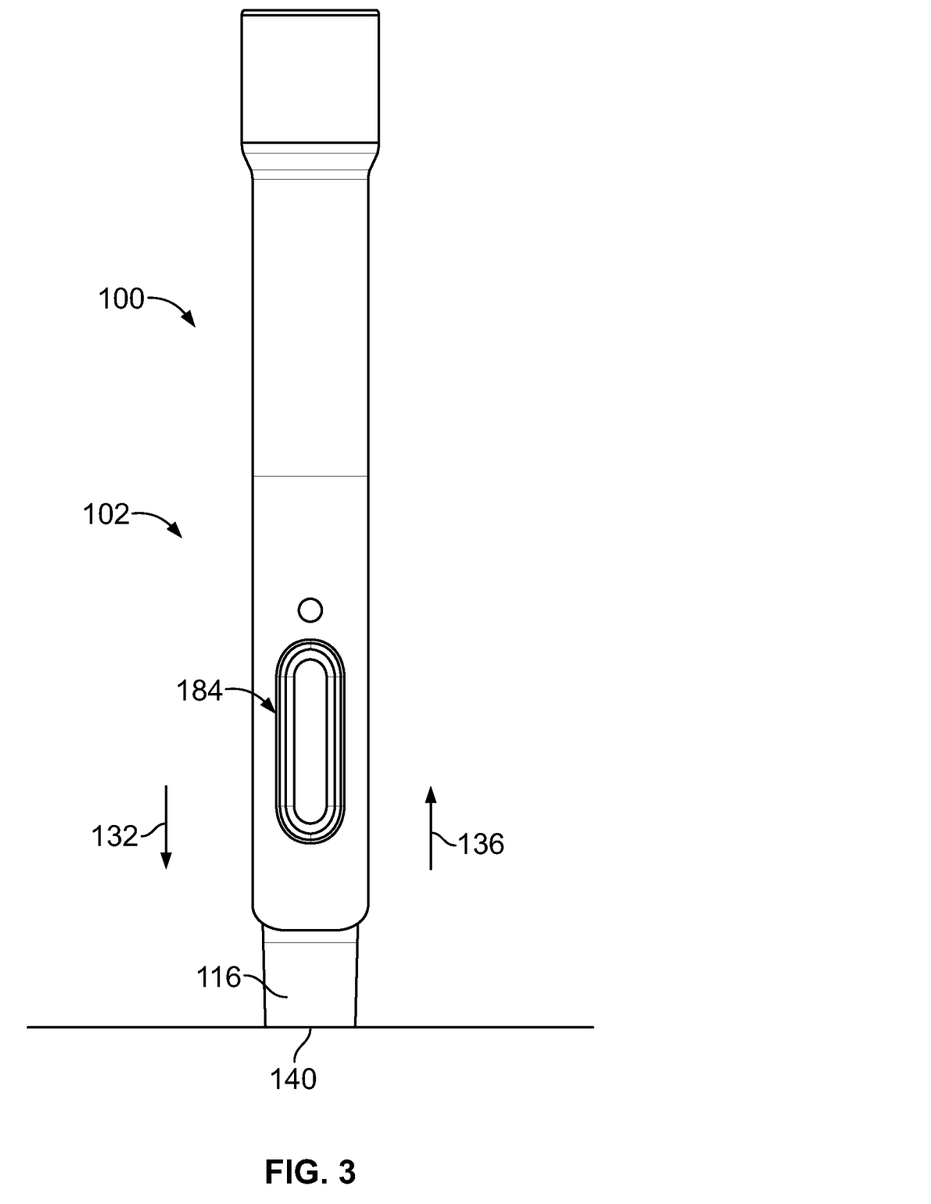
FIG. 3 illustrates a front view of the example drug delivery device of FIG. 1 during dose delivery, according to an example embodiment of the present disclosure.

In general, the valve 124 may be activated by the drug delivery device 100 in any suitable manner. In the example embodiment of FIG. 1, the needle cover 116 and the sleeve 126 interact with one another in order to activate the valve 124. To initiate the injection process, the user places the drug delivery device 100 on an injection site, such as injection site 140 as shown in FIG. 3. When the drug delivery device 100 is pressed onto the injection site 140 in distal direction 132, the needle cover 116 moves in a proximal direction 136 relative to the main housing 102. This retraction of the needle cover 116 exposes the needle 114 and the needle 114 is consequently inserted into the injection site 140.

In addition to exposing needle 114, this retraction of the needle cover 116 also serves to activate the valve 124 of the pneumatic power pack 120. In particular, the axial movement of the needle cover 116 in the proximal direction 136 causes axial movement of the sleeve 126 in the proximal direction 136. This axial movement of the sleeve 126 causes the sleeve 126 to interact with and activate the valve 124. The needle shield 116 may interact with sleeve 126 in any suitable manner in order to move the sleeve 126 in order to activate the valve 124. In the example shown in FIG. 2, a coupling flange 138 is attached to the sleeve 126. Axial movement of the needle shield 116 in the proximal direction 136 causes a proximal end 144 of the needle cover 116 to engage the coupling flange 138 and move the sleeve 126 in the proximal direction 136 to activate the valve 124.

The sleeve 126 may interact with the valve 124 in any suitable manner in order to activate the valve 124. In the example of FIG. 2, valve 124 includes a push portion 142 configured to open the valve 124. In particular, the valve 124 is configured to open when the push portion 142 is moved a threshold amount in the proximal direction 136. Axial movement of the sleeve 126 in the proximal direction 136 causes the sleeve 126 to contact the push portion 142 and then move the push portion 142 the threshold amount in the proximal direction 136. This movement opens the valve 124 and releases the pressurized gas 123. In general, for such a push-activated valve, any suitable threshold amount of movement in the proximal direction 136 to activate the valve 124 is possible. In an example, the threshold amount is between 0.5 and 5 millimeters (mm). However, threshold amounts less than 0.5 mm and greater than 5 mm are possible as well.

Although the example of FIG. 2 depicts a push-activated valve 124, in other example embodiments, the valve 124 may be activated in other suitable ways. For instance, the valve 124 may include a twist portion that is configured to open the valve 124 upon rotation. In such an example, the device 100 is configured such that movement of the sleeve 126 causes rotation of the twist portion to open the valve 124. Other examples are possible as well.

Figures 4, 5:
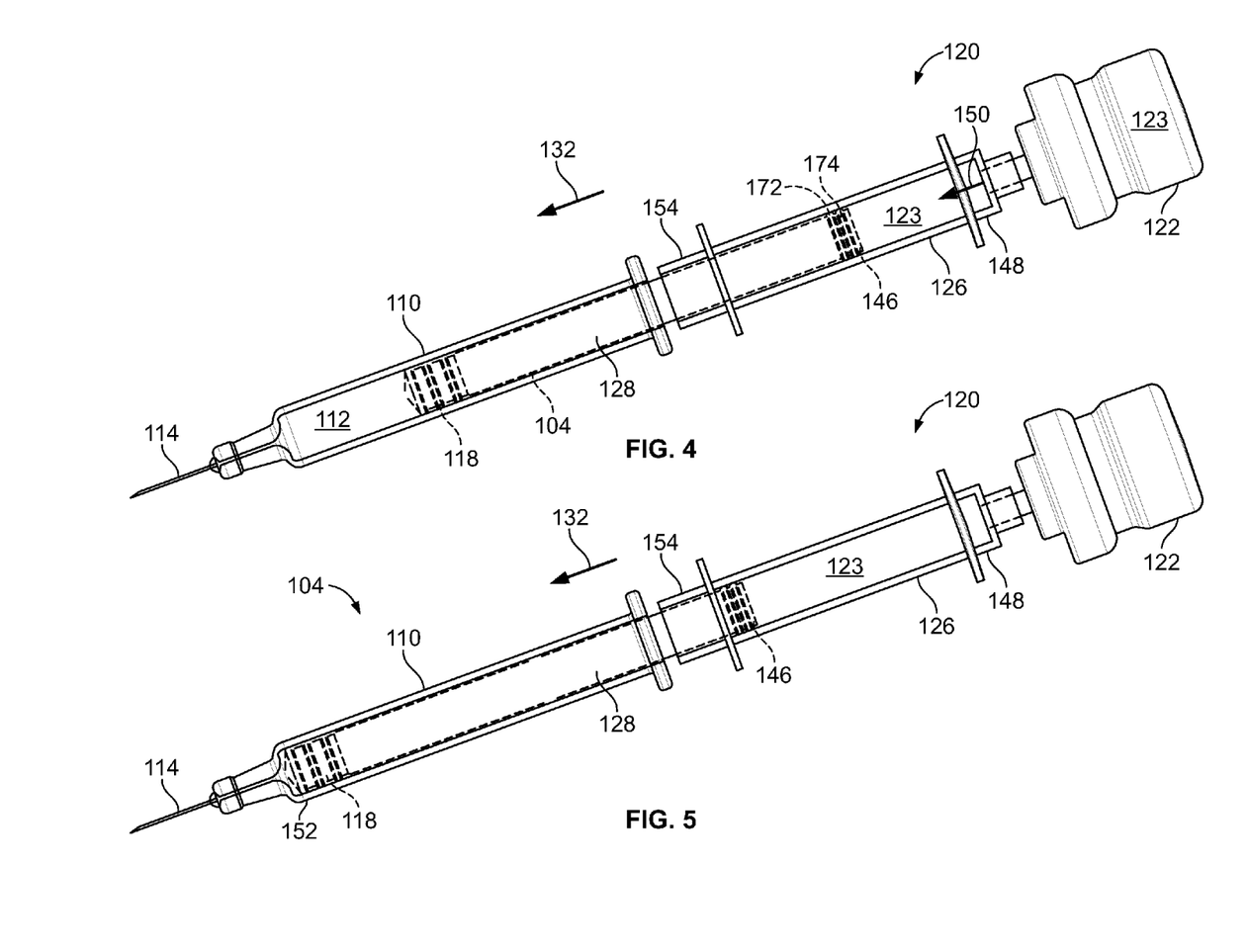
FIG. 4 illustrates a perspective view of example components of the drug delivery device of FIG. 1 during dose delivery, according to an example embodiment of the present disclosure.
FIG. 5 illustrates a perspective view of example components of the drug delivery device of FIG. 1 at the end of dose delivery, according to an example embodiment of the present disclosure.

After activation of the valve 124, the pneumatic power pack 120 releases the pressurized gas 123 to automatically inject the dose of medicament 112. The injection process is described in detail with reference to FIGS. 2 and 4-5. As mentioned above, FIG. 2 depicts the device 100 in an initial state prior to injection. Further, FIG. 4 depicts the pneumatic power pack 120 and syringe 104 during dose delivery. Still further, FIG. 5 depicts the pneumatic power pack 120 and syringe 104 at the end of dose delivery.

In the initial state (see FIG. 2), a proximal end 146 of plunger 128 is positioned in a proximal end 148 of the sleeve 126. When the valve 124 is activated, the valve 124 releases the pressurized gas 123. The pressurized gas 123 then flows into the sleeve 126 as indicated by arrow 150 (see FIG. 4) and propels the plunger 128 in distal direction 132 with respect to the sleeve 126 and syringe 104, so as to eject the medicament from the syringe 104 through the needle 114. Since sleeve 126 is in gas-tight engagement with the pressurized gas source 122 and the plunger 128 is in sliding gas-tight engagement with the inner wall of sleeve 126, the released pressurized gas 123 flowing into the sleeve 126 creates a pressure sufficient to propel the plunger 128 in the distal direction 132 with respect to the sleeve 126.

The pressurized gas 123 propels the plunger 128 in the distal direction 132 until the stopper 118 reaches a distal end 152 of the syringe body 110 (see FIG. 5). When the stopper 118 reaches the distal end 152 of the syringe body 110, the proximal end 146 of plunger 128 is positioned in a distal end 154 of sleeve 126.

During the dose delivery, the sleeve 126, syringe 104, and gas source 122 may be axially fixed with respect to main housing 102. As a result of these components being axially fixed during dose delivery, all or substantially all of the pressure from the released pressurized gas 123 will beneficially go towards propelling the plunger 128 in the distal direction 132.

Figures 6, 7:
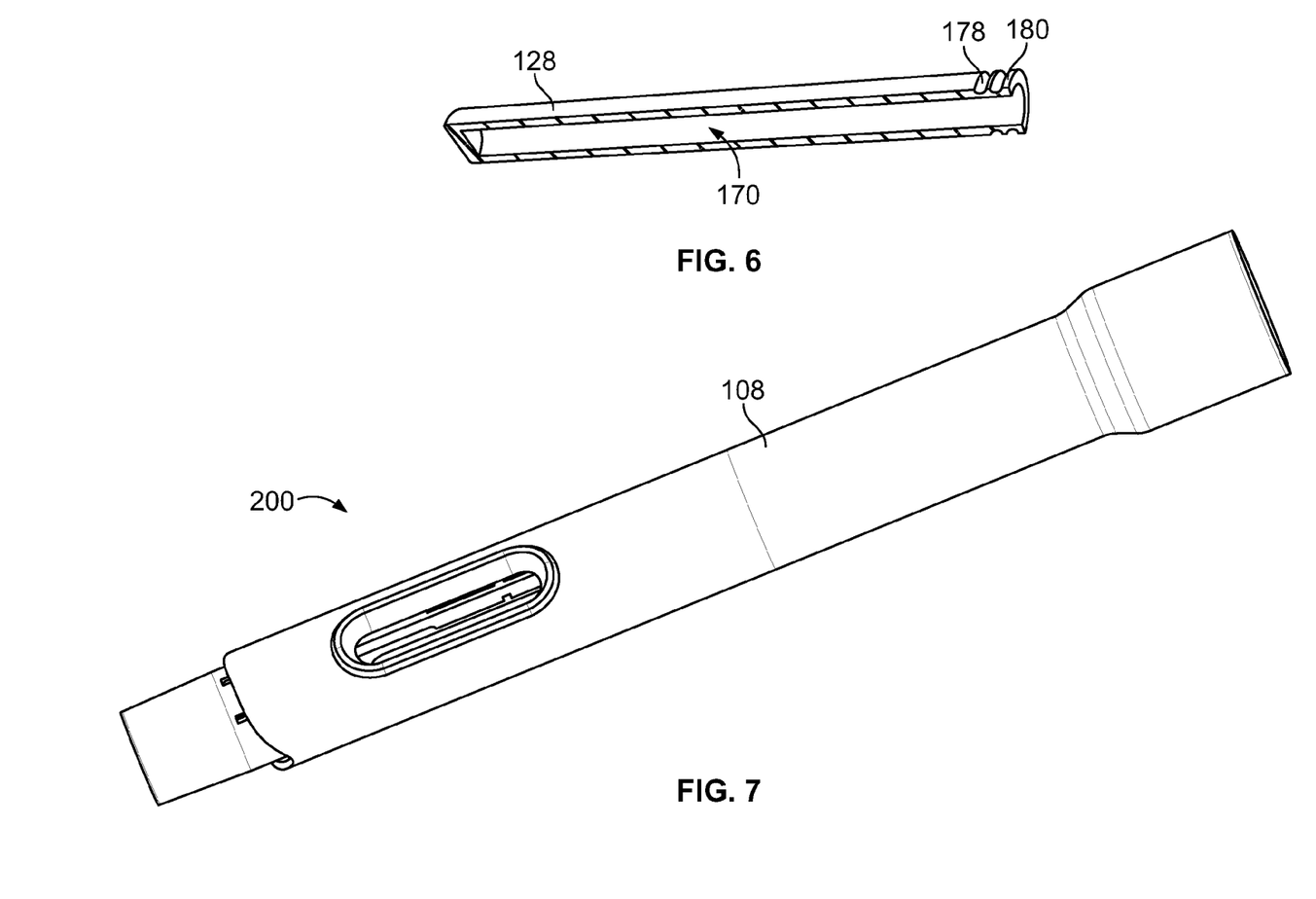
FIG. 6 illustrates a perspective, cross-sectional view of an example plunger of the drug delivery device of FIG. 1, according to an example embodiment of the present disclosure.
FIG. 7 illustrates a perspective view of an example drug delivery device having an example pneumatic power pack, according to an example embodiment of the present disclosure.

In an example embodiment, the plunger 128 includes an inner chamber configured to receive the pressurized gas 123. FIG. 6 illustrates a perspective cross-sectional view of plunger 128, which includes inner chamber 170. During dispense, the pressurized gas 123 flowing into sleeve 126 will also flow into the inner chamber 170 of the plunger 128. Beneficially, the plunger 128 including an inner chamber 170 may help to reduce the mass of the plunger 128, and this may consequently reduce the force required to propel the plunger 128 forward during dose delivery.

Although plunger 128 is depicted as having an open inner chamber 170 for receiving pressurized gas 123, in other example embodiments, the inner chamber is closed such that pressurized gas 123 does not flow into the inner chamber 170. Such a closed inner chamber 170 may help to reduce the mass of the plunger 128, and this may consequently reduce the force required to propel the plunger 128 forward during dose delivery. In yet other example embodiments, the plunger 128 does not include an inner chamber.

As mentioned above, sleeve 126 is in gas-tight engagement with pressurized gas source 122 and plunger 128 is in sliding gas-tight engagement with the inner wall 130 of sleeve 126. The gas-tight engagement between the sleeve 126 and gas source 122 may be provided in any suitable manner. For instance, the engagement between the sleeve 126 and gas source 122 may include at least one washer or O-ring to provide the gas-tight engagement. Similarly, the sliding gas-tight engagement may be provided in any suitable manner. For instance, at least one washer or O-ring may be attached to the plunger 128 to provide the sliding gas-tight engagement with the inner wall 130. As seen in FIG. 4, plunger 128 includes a first washer 172 and a second washer 174 attached at the proximal end 146 of the plunger 128. The plunger 128 may include one or more ribs, such as ribs 178 and 180 (see FIG. 6), to hold the washers 172, 174 on the plunger 128. The washers 172, 174 placed around the plunger 128 ensure that the space between the plunger 128 and pressurized gas source 122 is substantially air-tight so that any gas leakage that would reduce the thrusting force is minimized or prevented. Other methods for providing the gas-tight engagement between the sleeve 126 and gas source 122 and for providing the slidable, gas-tight engagement with inner wall 130 are possible as well.

After injection is complete, the device 100 is removed from the injection site 140 and the needle cover 116 will extend outward and lock into place. This extension and locking may limit or prevent needle stick injuries. The needle cover 116 may extend outward and lock into place in any suitable manner. In an example embodiment, when the drug delivery device 100 is removed from the injection site 140, the needle cover 116 automatically extends outward in the distal direction 132 under a force such as a spring force. As seen in FIG. 2, drug delivery device 100 includes spring 182 positioned between syringe 104 and needle cover 116. This spring 182 provides the force to automatically extend the needle cover 116 in the distal direction 132 after the user removes the drug delivery device 100 from the injection site 140. Other ways of locking the needle cover 116 in an extended position are possible as well.

In an example embodiment, during dose delivery, the user can hear and/or feel an audible and/or tactile feedback (e.g., clicking) throughout the dose delivery. For instance, the device 100 may include a clicker than produces a clicking sound when the plunger 128 is being propelled forward in the distal direction 132. The end of injection may be indicated by the audible/tactile clicking having stopped. Additionally or alternatively, the stopper 118 and plunger 128 may be visible in the main body window 184 (see FIG. 3) when injection is complete. In such an example, the end of delivery may be indicated by the stopper 118 and plunger 128 having stopped moving. Other indications of dose delivery being complete are possible as well.

Pressurized gas source 122 may be any source of pressurized gas suitable to propel the plunger 128 forward to eject the medicament 112. In an example embodiment, the pressurized gas is $CO_2$, Argon, or Nitrogen. Other example pressurized gases are possible as well. Further, in an example embodiment, the pressurized gas source 122 contains a gas pressurized to a pressure of between 50-3000 PSI. However, in other examples, the pressure may be less than 600 PSI or more than 3000 PSI. For instance, in another example, the pressure is between 500-600 PSI. In yet another example, the pressure is between 3000-3500 PSI. Other example pressures are possible as well.

Additionally, even though a syringe 104 is described in this example embodiment of FIG. 1, any suitable type of medicament container may be used in the disclosed drug delivery device 100, such as a syringe, an ampoule, a cartridge, an enclosure, etc. Further, the medicament may be any suitable substance used for medical treatment. In an example embodiment, the medicament is epinephrine (commonly known as adrenaline).

In an example embodiment, the disclosed pneumatic power pack may be configured to propel the plunger with a constant or substantially constant force. An example drug delivery device having a pneumatic power pack configured to propel the plunger with a constant or substantially constant force is described with reference to FIGS. 7-10.

FIG. 7 depicts a drug delivery device 200. The drug delivery device 200 operates in a similar fashion as drug delivery devices 100; however, rather than including power pack 120, drug delivery device 200 includes power pack 202 (see FIG. 8). Other elements of drug delivery device 200 may be the same or substantially similar to the other elements drug delivery device 100, and thus drug delivery device 200 is not described in as great of detail. It should be explicitly noted, however, that any possibilities and permutations described above with respect to drug delivery device 100 may equally apply to drug delivery device 200, and vice versa. Further, throughout the description of FIGS. 7-10, elements in drug delivery device 200 that are the same as or substantially similar to elements in drug delivery device 100 are described with like reference numerals.

Figure 8:
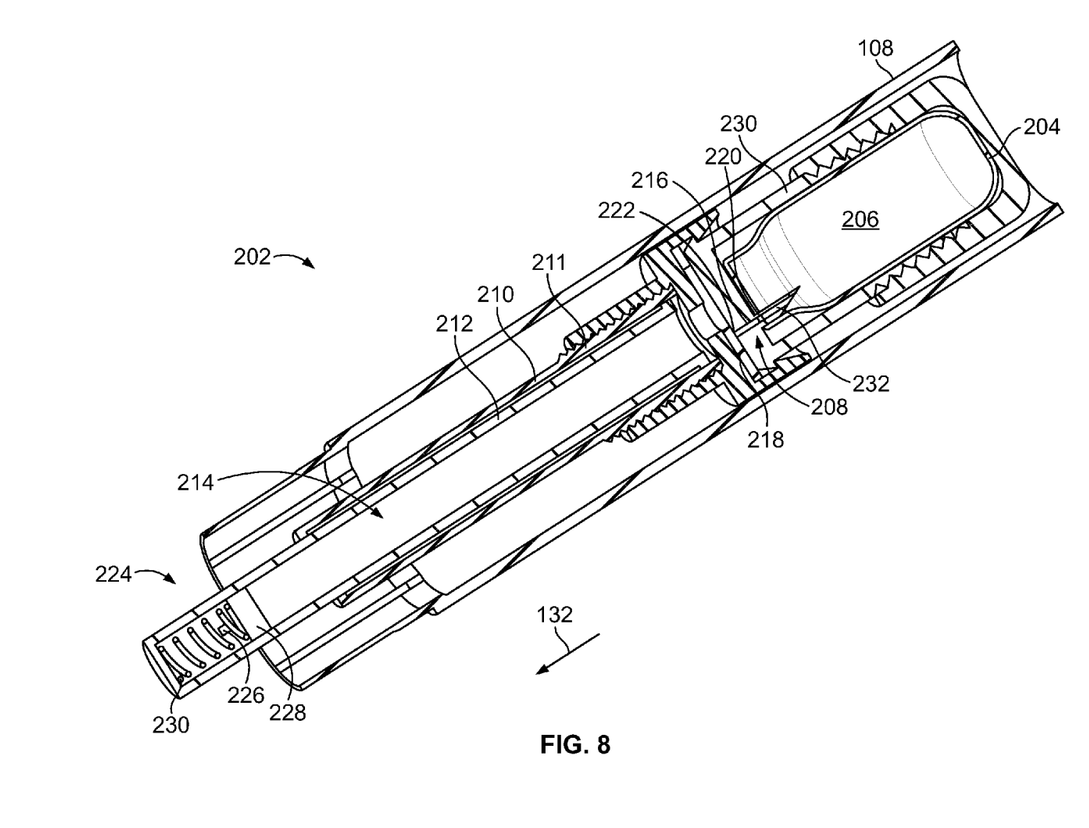
FIG. 8 illustrates a perspective, cross-sectional view of the pneumatic power pack of the drug delivery device of FIG. 7, according to an example embodiment of the present disclosure.

FIG. 8 depicts a cross-sectional view of power pack 202 of drug delivery device 200. Power pack 202 is positioned in second housing portion 108. Further, power pack 202 includes pressurized gas source 204 storing pressurized gas 206, valve 208, sleeve 210, and plunger 212 having inner chamber 214. Sleeve 210 is in gas-tight engagement with pressurized gas source 204 and plunger 212 is in sliding gas-tight engagement with an inner wall 211 of sleeve 210. In order to propel the plunger 212 with a constant or substantially constant force, valve 208 is configured to release the pressurized gas 206 at a substantially constant rate, and plunger 212 is configured to release pressure when the pressurized gas 206 in the inner chamber 214 reaches a threshold pressure level.

With reference to FIG. 8, valve 208 includes a flow control orifice 216. Valve 208 also includes a gasket 218 configured to open and close the flow control orifice 216. Flow control orifice 216 includes an opening 220 and an exit 222 and is sized to release pressurized gas 206 at a substantially constant rate regardless of the pressure at the opening 220 and the pressure at exit 222. An example size of the flow control orifice 216 may be on the order of 5 to about 250 Microns.

The flow control orifice 216 may release the pressurized gas at any suitable substantially constant rate. As mentioned herein, by the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

In an example embodiment, the substantially constant rate at which the flow control orifice 216 releases the pressurized gas is any substantially constant rate. Further, as used herein, a substantially constant rate of X means any rate in the range of $X+/-0.05*(X)$.

Figures 9, 10:
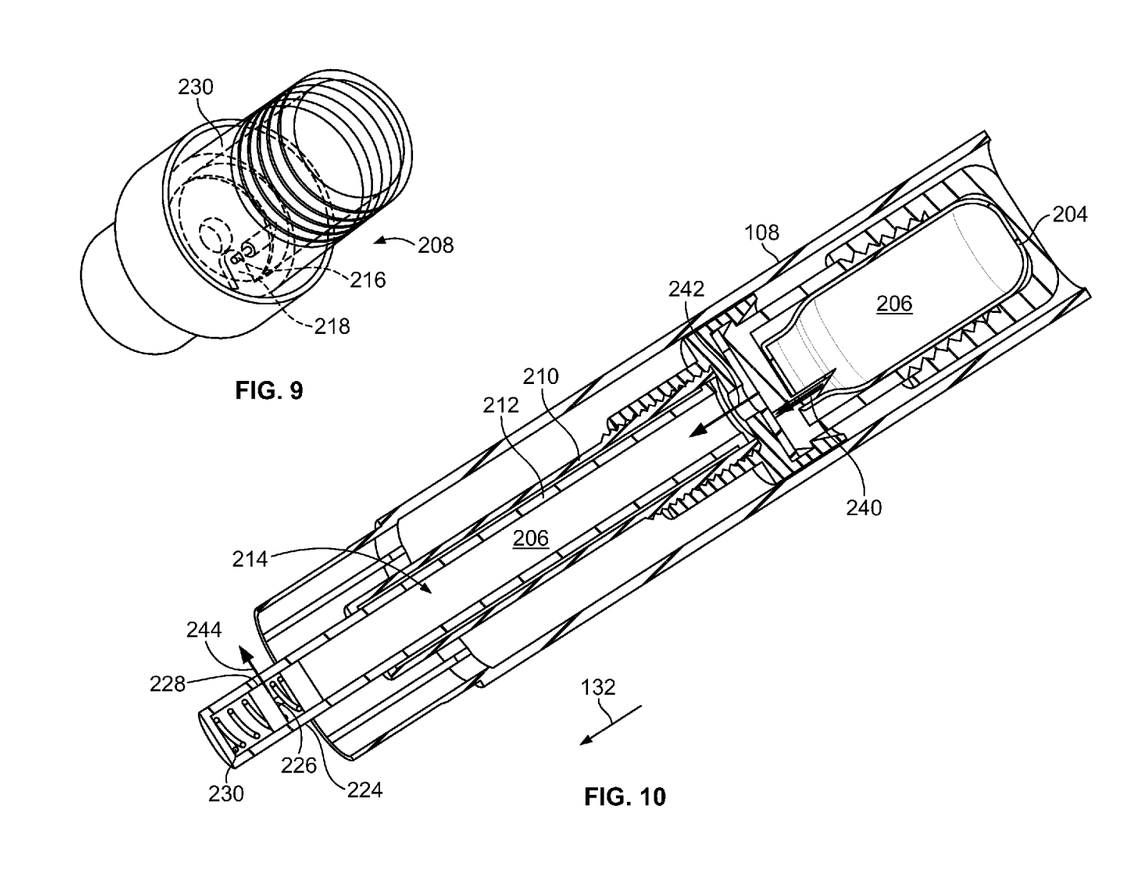
FIG. 9 illustrates a perspective view of an example valve of the pneumatic power pack of FIG. 8, according to an example embodiment of the present disclosure.
FIG. 10 illustrates a perspective, cross-sectional view of the pneumatic power pack of the drug delivery device of FIG. 7 during dose delivery, according to an example embodiment of the present disclosure.

Plunger 212 includes a pressure release valve 224 that is configured to release pressure when the pressurized gas in the inner chamber 214 reaches a threshold pressure level. The pressure release valve 224 includes one or more release holes (such as release hole 226), gasket 228, and spring 230. Gasket 228 and spring 230 are disposed in a distal end of inner chamber 214. When the pressure level in the inner chamber 214 is below the threshold pressure level, the gasket 228 is positioned at a location proximal to a location of the release hole 226, so as to prevent the pressurized gas 206 from reaching the release hole 226. FIG. 8 illustrates the gasket 228 positioned at a location proximal to a location of the release hole 226. On the other hand, when the pressure level in the inner chamber 214 is above the threshold level, the pressurized gas 206 urges the gasket 228 against the spring 230 in a distal direction 132 until the gasket 228 moves distally beyond at least a part of the release hole 226, so as to allow the pressurized gas 206 to exit the release hole 226. FIG. 10 depicts the gasket 228 positioned at a location distal of the release hole 226.

In general, the threshold pressure level may be selected based on a desired force at which the plunger 212 is to be propelled. In an example embodiment, the threshold pressure level is a pressure level between 25 PSI and 400 PSI.

In the example shown in FIG. 8, pneumatic power pack 202 includes a container 230 for holding the pressurized gas source 204. The container 230 includes a needle 232 that punctures the pressurized gas source 204 during assembly of the power pack 202. In this example embodiment, the valve 208 for the pressurized gas source 204 is provided by flow control orifice 216 in container 230 and gasket 218. However, in other embodiments, the pressurized gas source 204 may be replaced by a gas source that already has a release valve, such as valve 124.

During operation of the drug delivery device 200, valve 208 may be activated in any suitable manner. In the example of FIG. 8, the valve 208 is activated by rotation of the gasket 218 to uncover the flow control orifice 216. Similar to drug delivery device 100, movement of the needle cover 116 may act on the sleeve 210 to activate the valve 208. For instance, axial movement of needle cover 116 acts on sleeve 210 in order to rotate the gasket 218 in a clockwise direction 238 (see FIG. 9) to uncover the flow control orifice 216. In one arrangement, the sleeve 210 and an inner housing portion enclosing the gasket 218 are coupled during assembly. The needle cover 116 may act on either the sleeve 210 or the inner housing portion, depending on the designs, and the gasket 218 will be rotated by the inner housing portion to open and active the valve 208. In others words, the needle cover 116 can act either the sleeve 210 or the inner housing portion to active the valve 208.]

When the valve 208 is activated by the rotation of gasket 218 to uncover flow control orifice 216, the pressurized gas 206 moves through flow control orifice 216 at a substantially constant flow rate as shown by arrow 240 (see FIG. 10). The pressurized gas 206 then moves into sleeve 210 and inner chamber 214 as shown by arrow 242. Since the plunger 212 is in sliding gas-tight engagement with the inner wall 211 of the sleeve 210, the flow of gas shown by arrow 242 will increase the pressure in the sleeve 210 and inner chamber 214 to propel the plunger 212 forward in distal direction 132 so as to eject medicament 112. The pressurized gas 206 propels the plunger 212 in the distal direction 132 with the substantially constant force until the stopper 118 reaches the distal end 152 of the syringe body 110. When the plunger 212 reaches this final point, any remaining pressurized gas 206 will be released through the pressure release valve 224 until the pressurized gas source 204 is empty or substantially empty.

During the propelling of the plunger 212 in the distal direction 132, if the pressure in the inner chamber 214 exceeds the threshold level, the pressurized gas 206 will get released through pressure release valve 224 (as shown by arrow 244). This pressure release through pressure release valve 224 allows for effectively keeping the pressure in the inner chamber 214 at a substantially constant value. As a result of the pressure being regulated in this manner, the pneumatic power pack 202 is able to push the plunger 212 in the distal direction 132 with a substantially constant force produced by the pressure in the sleeve 210 and inner chamber 214.

The pneumatic power pack 202 may propel the plunger 212 forward with any suitable substantially constant force. As mentioned herein, by the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

In an example embodiment, the substantially constant force at which the plunger 212 is propelled is any substantially constant force falling in the range of forces between 10 N and 100 N+−15 N. Further, as used herein, a substantially constant force of X Newtons means any force in the range of 10 N and 100 N+−15 N.

Beneficially, the disclosed pneumatic power pack provides a cost effective means for propelling a plunger forward in an automatic injection device. Further, embodiments of the disclosed pneumatic power pack also provide a low-cost means for propelling the plunger forward at a substantially constant force. Therefore, the disclosed pneumatic power pack may help to reduce the cost of manufacturing automatic injection devices.

In the examples shown in the Figures, the drug delivery devices 100 and 200 are configured to inject a non-variable dose of medicament. However, in other embodiments, the drug delivery device could be configured to allow the user to select a variable single dose. For instance, in an example embodiment, the user is able to select two different dose values, three different dose values, four different dose values, and so forth.

In the Figures, various engagement features for are shown for providing an engagement between one or more components of the drug delivery device. The engagement features may be any suitable connecting mechanism such as a snap lock, a snap fit, form fit, a bayonet, lure lock, threads or combination of these designs. Other designs are possible as well.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

We claim:

1. A drug delivery device comprising:
   a main housing;
   a syringe arranged in the main housing, wherein the syringe comprises a medicament;
   a needle attached to the syringe;
   a needle cover axially movable with respect to the main housing; and
   a pneumatic power pack arranged in the main housing, wherein the pneumatic power pack comprises:
      (i) a pressurized gas source storing pressurized gas;
      (ii) a valve for the pressurized gas source;
      (iii) a sleeve having an inner wall, wherein the sleeve is configured to receive pressurized gas released from the pressurized gas source; and (iv) a plunger axially movable with respect to both the sleeve and the syringe, wherein the plunger is in sliding gas-tight engagement with the inner wall of the sleeve, wherein, upon activation of the valve, the valve releases the pressurized gas and the released pressurized gas flows into the sleeve and propels the plunger in a distal direction with respect to the sleeve and the syringe, so as to eject the medicament from the syringe, and wherein axial movement of the needle cover in the proximal direction causes axial movement of the sleeve in the proximal direction, and wherein the axial movement of the sleeve in the proximal direction activates the valve to release the pressurized gas.

2. The drug delivery device of claim 1, further comprising:

a coupling flange attached to the sleeve, wherein axial movement of the needle cover in the proximal direction causes the needle cover to engage the coupling flange and move the sleeve in the proximal direction.

3. The drug delivery device of claim 1, wherein the valve comprises a push portion configured to open the valve, and wherein axial movement of the sleeve in the proximal direction causes the sleeve to contact the push portion and open the valve.

4. The drug delivery device of claim 1, wherein the syringe comprises a stopper, and wherein movement of the plunger in the distal direction with respect to the sleeve and the syringe causes the plunger to act on the stopper.

5. The drug delivery device of claim 1, wherein the plunger comprises an inner chamber configured to receive the released pressurized gas.

6. The drug delivery device of claim 1, further comprising:

at least one washer attached to the plunger, wherein the at least one washer provides sliding gas-tight engagement with the inner wall of the sleeve.

7. The drug delivery device of claim 1, wherein the valve comprises:

a flow control orifice; and
a gasket configured to open and close the flow control orifice.

8. The drug delivery device of claim 7, wherein axial movement of the needle cover in the proximal direction causes rotation of the gasket to open the flow control orifice.

9. The drug delivery device of claim 7, wherein the pneumatic power pack further comprises a container for holding the pressurized gas source, wherein the container comprises (i) the flow control orifice and (ii) an additional needle configured to puncture the pressurized gas source.

10. The drug delivery device of claim 1, wherein the pneumatic power pack is configured to propel the plunger in the distal direction with respect to the sleeve and the syringe at a substantially constant force.

11. The drug delivery device of claim 10, wherein the valve comprises a flow control orifice having an opening and an exit, wherein the flow control orifice is sized to release the pressurized gas at a substantially constant rate in response to a pressure at the opening and a pressure at the exit.

12. The drug delivery device of claim 10, wherein the plunger comprises:

an inner chamber configured to receive the released pressurized gas; and a pressure release valve configured to release pressure when the received released pressurized gas in the inner chamber reaches a threshold pressure level.

13. The drug delivery device of claim 12, wherein the pressure release valve comprises:

at least one release hole; and a gasket and spring disposed in a distal end of the inner chamber, wherein the gasket and spring are configured such that (i) below the threshold pressure level, the gasket is positioned at a location proximal to a location of the at least one release hole, so as to prevent the released pressurized gas from reaching the at least one release hole, and (ii) above the threshold pressure level, the released pressurized gas urges the gasket against the spring in a distal direction until the gasket moves distally beyond at least part of the at least one release hole, so as to allow the received released pressurized gas to exit the at least one release hole.

14. The drug delivery device of claim 1, wherein the drug delivery device is a single-use disposable injection device.

15. A drug delivery device comprising:

a main housing;

a medicament container arranged in the main housing, wherein the medicament container comprises a medicament;

a needle cover axially movable with respect to the main housing; and a pneumatic power pack arranged in the main housing, wherein the pneumatic power pack comprises:

(i) a pressurized gas source having a valve and storing pressurized gas;

(ii) a sleeve having an inner wall, wherein the sleeve is axially moveable with respect to the main housing; and (iii) a plunger comprising an inner chamber, wherein the plunger is axially movable with respect to both the sleeve and the medicament container, wherein the plunger is in sliding gas-tight engagement with the inner wall of the sleeve, and wherein the sleeve and the inner chamber are configured to receive pressurized gas released from the pressurized gas source, wherein axial movement of the needle cover in a proximal direction causes axial movement of the sleeve in the proximal direction, wherein the axial movement of the sleeve in the proximal direction activates the valve to release the pressurized gas, and wherein the released pressurized gas flows into both the sleeve and the inner chamber and propels the plunger in a distal direction with respect to the sleeve and the medicament container, so as to eject the medicament from the medicament container.

16. A drug delivery device comprising:

a main housing;

a medicament container arranged in the main housing, wherein the medicament container comprises a medicament; and a pneumatic power pack arranged in the main housing, wherein the pneumatic power pack comprises:

(i) a pressurized gas source storing pressurized gas;
(ii) a valve for the pressurized gas source;
(iii) a sleeve having an inner wall; and
(iv) a plunger comprising an inner chamber and a pressure release valve configured to release pressure from the inner chamber when the pressure in the inner chamber reaches a threshold pressure level, wherein the plunger is axially movable with respect to both the sleeve and the medicament container, wherein the plunger is in sliding gas-tight engagement with the inner wall of the sleeve, wherein the sleeve and the inner chamber are configured to receive pressurized gas released from the pressurized gas source, wherein the valve is configured to release the pressurized gas upon activation of the valve, and wherein the released pressurized gas is configured to flow into both the sleeve and the inner chamber to propel the plunger in a distal direction with respect to the sleeve and the medicament container with a substantially constant force, such that the plunger moves into the medicament container to eject the medicament from the medicament container.

17. The drug delivery device of claim 16, wherein the pressure release valve comprises:

at least one release hole; and a gasket and spring disposed in a distal end of the inner chamber, wherein the gasket and spring are configured such that (i) below the threshold pressure level, the gasket is positioned at a location proximal to a location of the at least one release hole, so as to prevent the released pressurized gas from reaching the at least one release hole, and (ii) above the threshold pressure level, the released pressurized gas urges the gasket against the spring in a distal direction until the gasket moves distally beyond at least part of the at least one release hole, so as to allow the received released pressurized gas to exit the at least one release hole.

18. The drug delivery device of claim 17, wherein the valve comprises a flow control orifice having an opening and an exit, wherein the flow control orifice is sized to release the pressurized gas at a substantially constant rate regardless of a pressure at the opening and a pressure at the exit.

* * * * *